(12) United States Patent
Nakasuji et al.

(10) Patent No.: US 7,385,197 B2
(45) Date of Patent: Jun. 10, 2008

(54) ELECTRON BEAM APPARATUS AND A DEVICE MANUFACTURING METHOD USING THE SAME APPARATUS

(75) Inventors: Mamoru Nakasuji, Yokohama (JP); Nobuharu Noji, Zushi (JP); Tohru Satake, Chigasaki (JP); Takeshi Murakami, Tokyo (JP); Hirosi Sobukawa, Isehara (JP); Toru Kaga, Hachioji (JP); Masahiro Hatakayama, Fujisawa (JP)

(73) Assignee: Ebara Corporation, Tokyo (JP)

( * ) Notice: Subject to any disclaimer, the term of this patent is extended or adjusted under 35 U.S.C. 154(b) by 379 days.

(21) Appl. No.: 11/175,390

(22) Filed: Jul. 7, 2005

(65) Prior Publication Data

US 2006/0016989 A1 Jan. 26, 2006

(30) Foreign Application Priority Data

Jul. 8, 2004 (JP) ............................. 2004-201736
Jul. 21, 2004 (JP) ............................. 2004-213083
Aug. 26, 2004 (JP) ............................. 2004-246468

(51) Int. Cl.
*G01N 23/00* (2006.01)
*G01K 7/00* (2006.01)

(52) U.S. Cl. ...................... 250/310; 250/306; 250/307; 250/492.1; 250/492.2; 250/492.3

(58) Field of Classification Search ................. 250/310
See application file for complete search history.

(56) References Cited

U.S. PATENT DOCUMENTS

| | | | | |
|---|---|---|---|---|
| 3,961,190 A | * | 6/1976 | Lukianoff et al. | 250/310 |
| 4,983,834 A | * | 1/1991 | Lindmayer et al. | 250/581 |
| 5,097,127 A | * | 3/1992 | Hildenbrand et al. | 250/310 |
| 5,153,434 A | * | 10/1992 | Yajima et al. | 250/311 |
| 5,444,256 A | * | 8/1995 | Nagai et al. | 250/396 R |
| 5,670,782 A | * | 9/1997 | Sato | 250/310 |
| 6,140,644 A | * | 10/2000 | Kawanami et al. | 250/310 |
| 6,172,363 B1 | * | 1/2001 | Shinada et al. | 250/310 |
| 6,274,876 B1 | * | 8/2001 | Kawanami et al. | 250/492.22 |
| 6,291,823 B1 | * | 9/2001 | Doyle et al. | 250/308 |
| 6,608,308 B1 | * | 8/2003 | Takagi et al. | 350/311 |
| 6,787,772 B2 | * | 9/2004 | Ose et al. | 250/310 |
| 6,855,929 B2 | * | 2/2005 | Kimba et al. | 250/310 |
| 6,855,938 B2 | * | 2/2005 | Preikszas et al. | 250/396 R |
| 6,909,930 B2 | * | 6/2005 | Shishido et al. | 700/121 |

(Continued)

*Primary Examiner*—David Vanore
*Assistant Examiner*—Bernard Souw
(74) *Attorney, Agent, or Firm*—Westerman, Hattori, Daniels & Adrian, LLP.

(57) ABSTRACT

Disclosed is an electron beam apparatus, in which a plurality of electron beams is formed from electrons emitted from an electron gun 21 and used to irradiate a sample surface via an objective lens 28, said apparatus comprising: a beam separator 27 for separating a secondary electron beams emanating from respective scanned regions on the sample from the primary electron beams; a magnifying electron lens 31 for extending a beam space between adjacent beams in the separated plurality of secondary electron beams; a fiber optical plate 32 for converting the magnified plurality of secondary electron beams to optical signals by a scintillator and for transmitting the signals; a photoelectric conversion device 35 for converting the optical signal to an electric signal; an optical zoom lens 33 for focusing the optical signal from the scintillator into an image on the photoelectric conversion device; and a rotation mechanism 36 for rotating the photoelectric conversion device 35 around the optical axis.

5 Claims, 10 Drawing Sheets

U.S. PATENT DOCUMENTS

| | | |
|---|---|---|
| 7,138,629 B2 * | 11/2006 | Noji et al. .................. 250/311 |
| 7,157,703 B2 * | 1/2007 | Nakasuji et al. ............ 250/311 |
| 7,241,993 B2 * | 7/2007 | Nakasuji et al. ............ 250/310 |
| 2004/0000858 A1 * | 1/2004 | Hwang et al. .............. 313/440 |
| 2004/0084629 A1 * | 5/2004 | Preikszas et al. ....... 250/396 R |
| 2005/0194917 A1 * | 9/2005 | Yoshinaga .................. 315/371 |
| 2006/0016989 A1 * | 1/2006 | Nakasuji et al. ............ 250/310 |
| 2007/0228922 A1 * | 10/2007 | Nakasuji ..................... 313/364 |

* cited by examiner

ELECTRON BEAM APPARATUS AND A DEVICE MANUFACTURING METHOD USING THE SAME APPARATUS

BACKGROUND OF THE INVENTION

The present invention relates to an electron beam apparatus for making an inspection of a sample, such as a wafer, a mask, a reticle or a liquid crystal, for example, having a pattern with a minimum line width equal to or smaller than 0.1 µm formed thereon, with high throughput and high precision by irradiating an electron beam onto the sample, and also to a device manufacturing method using the same electron beam apparatus.

There has been well known such an electron beam apparatus that uses an electron beam in order to detect a defect on a sample, such as a semiconductor wafer or a mask, in a manner that a primary electron beam emitted from an electron gun is focused via an optical system into an image on the sample, secondary electrons emanating from the sample are detected to provide a secondary electron image, and finally the sample is evaluated based on thus obtained secondary electron image.

The method for irradiating the primary electron beam onto the sample in such an electron beam apparatus may include one method in which a multi-beam of primary electrons is formed and focused into an reduced image on the sample, while deflecting the multi-beam for scanning the sample surface or while providing the irradiation of the multi-beam across a relatively large area on the sample at once. The method for detecting the secondary electrons emanating from the scanned region or the irradiated region on the sample as the result of the electron beam irradiation includes one method using an image projection optical system which can provide a magnified projection image of the secondary electrons covering a relatively large area onto a detection surface so as to carry out the detection of the secondary electrons. In that detection method, for example, the secondary electrons are focused into an image in an entrance of a MCP or the like and converted to an optical signal by a scintillator or the like, and then an image of resultantly multiplied secondary electrons from the MCP is converted to an optical signal by the scintillator and guided onto a detector, such as a CCD, via a FOP (Filter Optic Plate), where the optical signal is converted to an electric signal to provide the secondary electron image.

The conventional electron beam apparatus as described above is, however, suffered from the following problems.

(1) When employing one type of optical system operable for converging both of the primary electron beam and the secondary electron beam simultaneously in an uniform magnetic field, there is a fear from the reason of a narrow beam spacing in the multi-beam used for the scanning operation that all of the secondary electrons forming a single secondary electron beam are not received in a single beam detector arranged for the detection of said secondary electron beam but a part of signal from said secondary electron beam could be get mixed onto any adjacent beam detectors.

(2) Although an electromagnetic lens of said image projection optical system normally produces a small magnitude of aberration along an optical axis, if the primary electron beam is deflected for the scanning over the sample, it could occasionally enter the lens at an angle in a position off from the optical axis, adversely enhancing the aberration. Further, the image projection optical system, if attempting to enlarge the field of view, could resultantly reduce transmission of the secondary electron and again adversely enhance the aberration. Further disadvantageously, the image projection optical system is likely to suffer from a problem of distortion that could be induced in association with a magnifying lens placed in a second and subsequent steps.

(3) Although some type of CCD implementing a surface detector may include an element having an exposure time as short as 5 µs, it is typically time-consuming when extracting data.

(4) From the fact that the spacing between the MCP and the scintillator may produce a blured beam on the order of 30 µm, it is required that a pixel on the sample should be enlarged sufficiently over said blur of 30 µm. To address this, it is required to employ an image projection optical system having an optical path as long as 1000 mm, but unfortunately the space charge effect from such a long optical path could adversely enhance the blur of the beam and the same image projection optical system is expensive, as well.

(5) The arrangement of the FOP and the CCD that have been optically adhered to each other makes the maintenance difficult.

(6) As for the irradiation optical system serving for irradiating an electron beam onto the sample, which is required to determine two different focal conditions, one for a crossover image and the other for a shaping aperture image, the system must have the optical path as long as 500 mm and ends up in an expensive system.

(7) For the case employing an immersion-type magnetic lens characterized by a reduced axial chromatic aberration as an objective lens, there has been no optical axis adjusting method developed for controlling a primary optical beam emitted from the field away from the optical axis so as to pass through an NA aperture. Therefore, it is difficult to reduce the aberration in the image projection optical system satisfactorily.

(8) There has been no method established for designing an objective lens comprising a deflection coil to satisfy the MOL (Moving Objective Lens) condition by using the immersion-type magnetic lens.

The present invention has been made in the light of the above lined-up current situations, and an object thereof is to provide an electron beam apparatus that can overcome the above problems.

Another object of the present invention is to provide a device manufacturing method directed to improve an inspection precision and throughput by using the above-designated electron beam apparatus to inspect a semiconductor device in the course of its manufacturing or as a finished product.

SUMMARY OF THE INVENTION

In Order to solve the above problems, according to an aspect of the present invention, there is provided an electron beam apparatus comprising: an electron source for irradiating a plurality of primary electron beams onto a sample surface; a scanning deflector for performing a scanning operation with the plurality of primary electron beams across the sample surface; an electron lens operable to converge the plurality of primary electron beams onto the sample surface, and also to converge secondary electrons emanating from respective scanned regions on the sample surface onto a detection surface, respectively; an electric field generation controller for generating an electric field between the electron source and the detection surface; an optical output converter for converting a plurality of secondary electron images that have been converged onto the detection surface to optical signals; and a photoelectric conversion device for converting the optical signal to an electric signal. Preferably, the electric field generator generates an electric field in a direction approximately at a right angle relative to a field generated by the electron lens.

According to the present aspect, since the electric field is applied between the electron source and the detection surface, it becomes possible to arrange the electron source and the detection surface with a longer distance therebetween, which facilitates the detection of the secondary electrons.

According to another aspect of the present invention, there is provided an electron beam apparatus comprising: an electron irradiation optics for irradiating a plurality of primary electron beams onto a sample surface; a scanning deflector for performing a scanning operation with the plurality of primary electron beams across the sample surface; an electron lens operable to converge secondary electrons emanating from respective scanned regions on the sample surface onto a detection surface, respectively; an optical output converter for converting a plurality of secondary electron images that have been converged onto the detection surface to optical signals, respectively; and a photoelectric conversion device having a plurality of light-sensitive surfaces, each of the light-sensitive surfaces arranged in a geometry and a position so as to make it possible to optically receive each of the optical signals from the plurality of secondary electron images distributed corresponding to the extent of scanning with the plurality of primary electron beams.

According to the present aspect, the secondary electron beams travels across the detection surface by the scanning operation with a plurality of primary electron beams. Typically, the travel extent of the secondary electron beam is wider than the scanning width of the primary electron beam. In conjunction with this traveling, the optical signals that have been converted from the secondary electron beams by the optical output converter are also distributed over the corresponding extent. Since each of the light-sensitive surfaces of the photoelectric converter is arranged in the geometry and the position that allows for the optical acceptance of each of thus distributed optical signals, the overlapping of detection areas could be avoided. In other words, the primary electron beam is allowed to make the scanning operation over the extended range. The geometry of the light-sensitive surface may include a rectangular shape extending in the direction corresponding to the scanning direction, for example. Further, making an adjustment to the position of each light-sensitive surface can achieve the optimal positioning of the light-sensitive surface by taking an effect from the rotation of the secondary electron beam due to the magnetic field into account.

According to yet another aspect of the present invention, there is provided an electron beam apparatus comprising: an electron irradiation optics for irradiating a plurality of primary electron beams onto a sample surface; a scanning deflector for performing a scanning operation with the plurality of primary electron beams across the sample surface; an electron lens operable to converge secondary electrons emanating from respective scanned regions on the sample surface onto a detection surface, respectively; an optical output converter for converting a plurality of secondary electron images that have been converged onto the detection surface to optical signals; a photoelectric conversion device for converting the optical signal to an electric signal; and a photoconduction path for guiding the optical signal output from the optical output converter to the photoelectric conversion device, said photoconduction path having light-sensitive areas, each configured in a geometry capable of optically receiving the optical signals distributed corresponding to the extent of scanning with the plurality of primary electron beams, respectively.

According to the present aspect, the electron beam apparatus employs the photoconduction path for guiding the optical signal output from the optical output converter to the photoelectric conversion device. Since the photoconduction path has the light-sensitive areas, each configured in such a geometry that is capable of optically receiving the optical signals distributed corresponding to the extent of scanning with the plurality of primary electron beams, respectively, the apparatus can accommodate the travel of the optical signals by the a plurality of primary electron beams and thus the overlapping of the detection areas is avoided, as is the case with the previously-discussed aspect. The geometry of the light-sensitive surface may includes a rectangular shape extending in the direction corresponding to the direction of scanning, for example.

According to still another aspect of the present invention, there is provided an electron beam apparatus comprising: an electron irradiation optics for irradiating a primary electron beam onto a sample surface; a scanning deflector for performing a scanning operation with the primary electron beam across the sample surface; an beam separator for separating a secondary electron beam emanating from a scanned region on the sample from the primary electron beam; a magnifying electron lens for magnifying the secondary electron beam that has been separated by the beam separator; an optical output converter for converting the magnified secondary electron beam to an optical signal; a photoelectric conversion device for converting the optical signal to an electric signal; and an optical zoom lens for focusing the optical signal from the optical output converter into an image on the photoelectric conversion device.

According to the present aspect, even through the pitch between secondary electron beams and thus the pitch between the optical signals are different from the design values, the adjustment by using the optical zoom lens, if applied to the magnification scale, can set the optical signals to be in consistency with the pitch between the photoelectric conversion devices. This can help prevent the overlapping and/or the missing of the detection areas.

According to still another aspect of the present invention, there is provided an electron beam apparatus comprising; an electron irradiation optics for irradiating a primary electron beam onto a sample surface; a scanning deflector for performing a scanning operation with the primary electron beam across the sample surface; a beam separator for separating a secondary electron beam emanating from each scanned region on the sample from the primary electron beam; a magnifying electron lens for magnifying the secondary electron beam that has been separated by the beam separator; an optical output converter for converting the magnified secondary electron beam to an optical signal; a photoelectric conversion device for converting the optical signal to an electric signal; and a rotation mechanism for rotating the photoelectric conversion device around an optical axis.

According to the present aspect, even through the rotational amount of the used electromagnetic lens is different from its design value and thus the orientation of the secondary electron images does not match the orientation of the photoelectric conversion device, the adjustment by using the rotation mechanism, if applied to the rotational position of the photoelectric conversion devices, can achieve the orientation alignment easily.

According to still another aspect of the present invention, there is provided an electron beam apparatus comprising: an electron irradiation optics for irradiating a plurality of primary electron beams onto a sample surface; a scanning deflector for performing a scanning operation with the plurality of primary electron beams across the sample surface; a beam separator for separating secondary electron beams emanating from respective scanned regions on the sample from the primary electron beam; a magnifying electron lens for magnifying a distance between any two beams of the plurality of secondary electron beams that have been separated by the beam separator; an optical output converter for converting the plurality of magnified secondary electron beams to optical signals; a photoelectric conversion device for converting the optical signal to an electric signal; an optical magnifying lens for magnifying the optical signal from the optical output converter into an image on the photoelectric conversion device; and a multi-aperture plate disposed in front of the photoelectric conversion device and having a plurality of apertures formed therethrough, said aperture having an aperture area that is small in the vicinity of an optical axis but is large in a peripheral region.

According to the present aspect, since the multi-aperture plate is disposed in front of the photoelectric conversion device, which has a plurality of apertures, each having the aperture area that is small in the vicinity of the optical axis but is large in the peripheral region, it can help compensate for the deteriorated secondary electron signal intensity due to the deteriorated off-axis intensity of the electron irradiation optics and/or the deteriorated signal of the secondary electron enlarged image due to the aberration from the secondary optical system.

According to still another aspect of the present invention, there is provided an electron beam apparatus comprising: an electron irradiation optics for irradiating a primary electron beam onto a sample surface; a scanning deflector for performing a scanning operation with the primary electron beam across the sample surface; an optical system including an at least one-stage of lens for converging the primary electron beam onto the sample surface and for converging secondary electrons emanating from the scanned region on the sample surface onto a detection surface; and an MOL motion deflector for driving a lens of the optical system positioned proximally to the sample to perform the MOL motion in synchronization with the scanning operation by the scanning deflector.

According to the present aspect, owing to the MOL motion, or the motion in which the optical axis of the lens positioned proximal to the sample, preferably that of the objective lens, that may be positioned most proximal to the sample, can be driven electro-magnetically to perform the MOL motion in synchronization with the scanning operation, such an aberration that could be induced by the primary electron beam or the secondary electron beam entering the location off from the optical axis during the scanning operation can be reduced, and consequently the higher resolution of the primary electron beam and thus the highly efficient detection of the secondary electron beams can be provided.

According to still another aspect of the present invention, there is provided an electron beam apparatus comprising: an electron irradiation system for irradiating a primary electron beam onto a sample surface; a magnification projection optical system for projecting secondary electrons emanating from the sample onto a detection surface in a magnified scale; an optical output converter for converting the electron image projected on the detection surface to an optical signal; and a detection device having a plurality of light-sensitive surfaces which is exposed to the optical signal from the optical output converter, wherein during at least one of the light-sensitive surfaces is being exposed to the optical signal, image data is transferred sequentially from other light-sensitive surfaces that have been exposed to the optical signal. Preferably, the electron beam apparatus further comprises a deflector for deflecting the secondary electrons so that the secondary electrons are sequentially projected in respective areas on the detection surface in a magnified scale, each of the areas corresponding to each one of the plurality of light-sensitive surfaces.

According to the present aspect, since the detection device having a plurality of light-sensitive surfaces to be exposed to the light signal is provided so that the image data may be transferred sequentially from each of the light-sensitive surfaces that has been exposed to the light signal, therefore the total time required to extract the image data from the detector can be reduced. This may help improve the throughput of the electron beam apparatus.

According to still another aspect of the present invention, there is provided an electron beam apparatus in which a field of view on the sample subject to irradiation of an electron beam is segmented into a plurality of sub-fields, and an electron image is obtained by each of the sub-fields so as to provide the final evaluation by an entire field on the sample, said apparatus comprising: an irradiation optical system for focusing an electron beam into an image by each of the sub-fields on the sample surface; an image projection optical system for focusing secondary electrons emanating from the sample into an image by each of the sub-fields on a detection surface; and an exposure controller for controlling an exposure time for each of the sub-fields to the detection surface in dependence on a distance from an optical axis of the image projection optical system to the each sub-field.

According to the present aspect, the exposure time per each sub-field to the detection surface can be controlled to be variable in dependence on the distance from the optical axis of the image projection optical system to the sub-field. For example, the control may be carried out in such a manner that the exposure time may be set longer for the sub-field distant from the optical axis, which has typically a smaller amount of light, but the exposure time may be set shorter for the sub-field close to the optical axis, which has typically a larger amount of light. This variable control can achieve the uniform S/N ratio of the secondary electron image over the entire field.

According to still another aspect of the present invention, there is provided an electron beam apparatus in which a field of view on the sample subject to irradiation of an electron beam is segmented into a plurality of sub-fields, and an electron image is obtained by each of the sub-fields so as to provide the final evaluation by an entire field on the sample, said apparatus comprising: an irradiation optical system for focusing an electron beam into an image by each of the sub-fields on the sample surface via an objective lens, wherein the electron beam is irradiated onto the sample surface at an angle relative to a normal line of the sample surface in the sub-field distant from an optical axis of the irradiation optical system, so that secondary electrons emanating from the sub-field can enter the objective lens in the vicinity of the optical axis thereof; and an image projection optical system for focusing the secondary electrons into an image on a detection surface.

In the present aspect, since the secondary electrons are incident in the objective lens in the vicinity of the optical axis thereof, the aberration from the optical system can be reduced.

According to still another aspect of the present invention, there is provided an electron beam apparatus in which a field of view on the sample subject to irradiation of an electron beam is segmented into a plurality of sub-fields, and an electron image is obtained by each of the sub-fields so as to provide the final evaluation by an entire field on the sample, said apparatus comprising: an irradiation optical system for focusing an electron beam into an image by each of the sub-fields on the sample surface; and an image projection optical system for focusing secondary electrons emanating from the sample into an image by each of the sub-fields on a detection surface, in which an auxiliary lens is disposed in front of a lens in the last-stage of the image projection optical system so that an image of crossover produced by a lens system positioned upstream to the auxiliary lens can be formed in the proximity to a principal plane of the lens in the last-stage.

According to the present aspect, since the image of crossover produced by the lens positioned upstream to the auxiliary lens can be formed in the proximity to the principal plane of the lens in the last-stage, the distortion and the transverse chromatic aberration and/or rotation in the image projection optical system can be reduced.

According to still another aspect of the present invention, there is provided an electron beam apparatus comprising: an irradiation optical system for focusing a primary electron beam into an image on a sample surface via an objective lens; an image projection optical system for focusing secondary electrons emanating from the sample into an image on a detection surface; an optical output converter for converting the secondary electron image formed by the image projection optical system to an optical signal; and an optical member for extracting the optical signal into an atmosphere side, in which a plane disposed in a vacuum side of the optical member defines an optical output converter and an output surface of the optical signal disposed in the atmosphere side defines a curved surface. Preferably, the optical output converter is a scintillator and the curved surface of the optical member may be convexly curved in a semi-spherical shape, a paraboloid of revolution or a hyperboloid of revolution in order to obtain the magnified image.

According to the present aspect, if the optical system has been configured to magnify the secondary electron image, the optical path could be made longer without the need for the MCP or the FOP. This facilitates a maintenance of the image projection optical system, and allows to fabricate the system with low cost.

According to still another aspect of the present invention, there is provided an electron beam apparatus comprising: an irradiation optical system for focusing a primary electron beam into an image on a sample surface via an objective lens; an image projection optical system for focusing secondary electrons emanating from the sample into an image on a detection surface; and at least one deflector cooperating with the objective lens to focus the secondary electrons emanating from a field distant from an optical axis into an image on the optical axis.

According to the present aspect, it has become possible to control the principal ray emitted from the field distant from the optical axis to be directed through the NA aperture.

According to still another aspect of the present invention, there is provided an electron beam apparatus comprising: an irradiation optical system for shaping and focusing an electron beam emitted from an electron gun into an image on a sample surface via an objective lens, said irradiation optical system including at least two-stage of lenses for focusing a light source image of the electron gun into an image on a principal plane of the objective lens, while focusing the shaped electrons image into an image on the sample; and an image projection optical system for focusing secondary electrons emanating from the sample or electrons transmitted through the sample into an image on a detection surface.

According to the present aspect, the image would not be formed between at least two-stage of lenses but the image of the shaping aperture is formed on the sample surface while satisfying the Koehler illumination condition. Therefore, it is no more necessary to intensify the excitation or magnetic excitation of each lens, which favorably helps reduce the size of the lens and the optical path length of the irradiation optical system.

According to still another aspect of the present invention, there is provided an electron beam apparatus comprising: an irradiation optical system for focusing a primary electron beams into an image on a sample surface via an objective lens; an image projection optical system including at least two-stage of deflectors, an magnifying lens and an NA aperture for detecting secondary electrons emanating from the sample; a wobbler application circuit for applying a wobbler to an exciting or an excitation voltage of the magnifying lens subject to an axial alignment; an image formation system for forming an image separated by the wobbler in synchronization with the x- and y-directional scanning according to a signal from the electron beam transmitted through the NA aperture, while carrying out the x- and y-directional scanning by at least one of the deflectors in the at least two-stage of deflectors; and a deflector controller operable to control the other of said at least two-stage of deflectors to minimize the separation of the image for the purpose of adjusting the optical axis so that a principal ray having exited from the objective lens is directed through a central region of the magnifying lens and through the NA aperture.

According to the present aspect, by minimizing the separation of the image produced by the image formation system, it becomes possible to provide the adjustment to the optical axis so that the principal ray having exited from the objective lens can be directed through the center of the magnifying lens and through the NA aperture. It is also contemplated that the wobbler application circuit, the image formation system and the deflector controller of the present aspect may be incorporated at least either one of the above-disclosed other aspects of the present invention in its allowable range.

At least either one of the objective lens defined in the above-disclosed respective aspects is the objective lens comprises: a magnetic lens including an inner magnetic pole and an outer magnetic pole with a magnetic gap produced by said inner and said outer magnetic poles defined in the sample side; a pipe made of ferrite and disposed inside the inner magnetic pole; and a deflector disposed inside the pipe made of ferrite.

According to the above aspect, such an objective lens could be provided by using an immersion-type magnetic lens that comprises a deflection coil to satisfy the MOL condition. If the deflector activates the MOL motion, or moves the optical axis of the objective lens magnetically in synchronization with the scanning operation, the aberration resultant from the primary or secondary electron beam entering the region off from the optical axis during the scanning operation could be reduced, so that the higher resolution of the primary electron beam and the highly efficient detection of the secondary electron beam could be achieved.

The aspect of the present invention for enabling the MOL motion can be applied not only to the electron beam apparatus but also to a general apparatus employing a charged particle beam, in this aspect, provided is an apparatus for evaluating a sample, in which a surface of the sample is scanned with a primary charged particle beam and secondary charged particles emanating from or transmitted through the sample are projected by an at least one-stage of lens onto a detection surface so as to provide the evaluation of the sample based on a detection image, wherein a lens positioned proximal to the sample is driven to make the MOL motion to reduce an aberration from the primary charged particle beam or an aberration from the secondary charged particle beam.

An electron beam apparatus according to any one of the above-disclosed aspects of the present invention may be used in a device manufacturing method for providing an evaluation of a sample represented by a wafer in the course of manufacturing or as a finished product.

Those and other advantages and effects of the present invention would be further apparent from the detailed description of the invention with reference to the attached drawings, as will be described below.

BRIEF DESCRIPTION OF THE DRAWINGS

FIG. 1(e) is a schematic diagram showing a detection section of the electron beam apparatus according to a second embodiment:

DETAILED DESCRIPTION OF THE INVENTION

First to Third Embodiment

Figure 1:
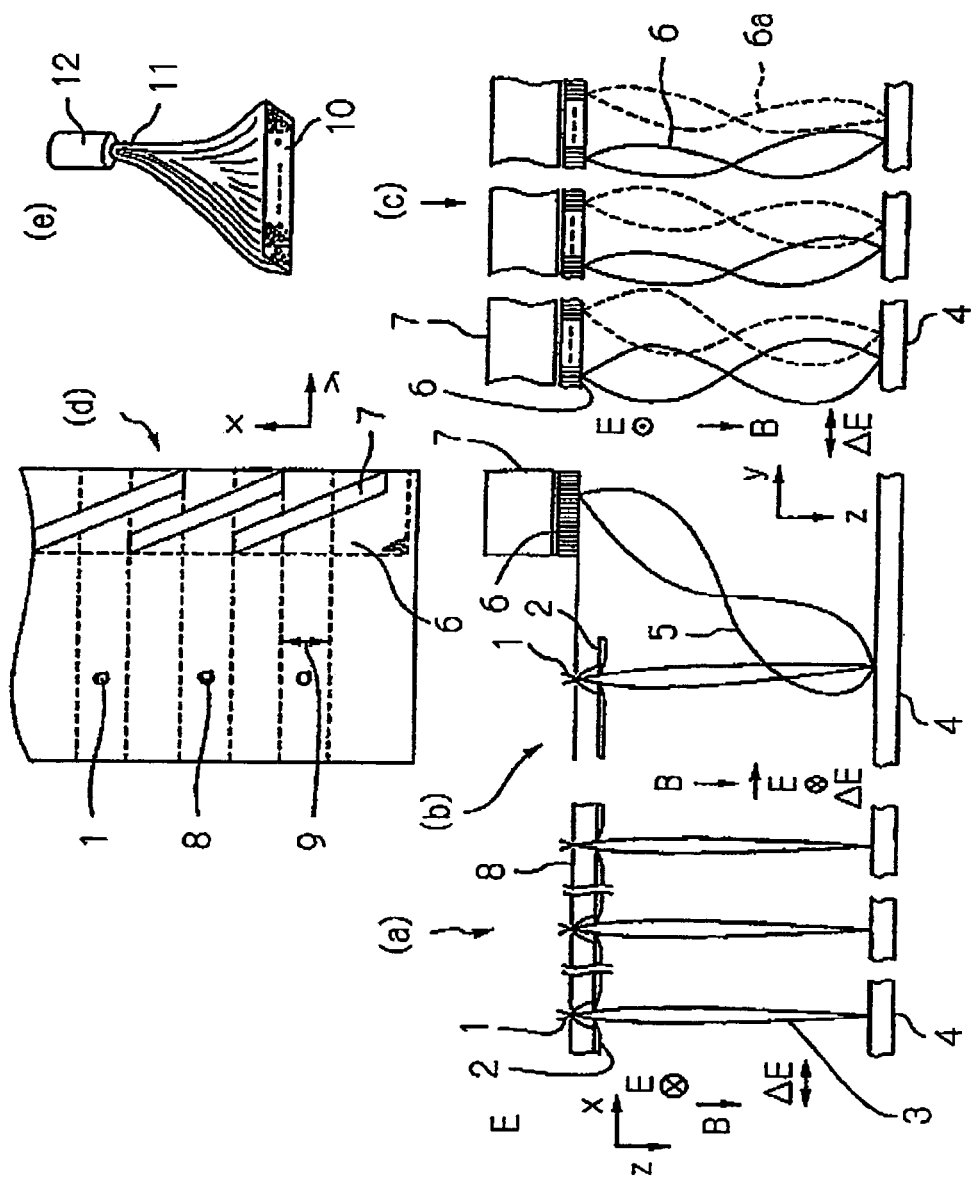
FIG. 1 is a schematic drawing depicting a configuration of an electron beam apparatus according to a first to a third embodiment of the present invention, wherein FIGS. 1(a), (b), (c) and (d) are side elevational views of the electron beam apparatus looking from four different directions, respectively

FIGS. 1(a), (b), (c) and (d) are side elevational views of the electron beam apparatus according to a first embodiment of the present invention, looking from four different directions, respectively. The electron beam apparatus comprises a multi-emitter 8 serving as an electron source for emitting primary electrons, a multi-aperture plate 2 having a plurality of small apertures, a lens configured so as to generate a magnetic field of uniform intensity in the z direction (along the optical axis) between the multi-aperture plate 2 and a sample 4, an electrostatic deflector that is not shown but operable to apply a deflecting electric field within the x-y plane for driving an irradiation spot of the primary electron beam that has been focused into an image by said lens on the sample 4 and thereby to scan the sample surface, a FOP (Fiber Optical Plate) 6 comprising a scintillator applied to a front surface thereof for converting electrons to light and a bundle of optical fibers capable of transmitting the converted light, and a photo multiplier (referred to PMT in abbreviation) 7 for detecting the intensity of the light that has been transmitted from the FOP.

The multi-emitter 1 is constructed in the FS-shape in a central location of the control electrode 8. The respective apertures of the multi-aperture plate 2 are spaced equally by a distance on the order of 200 µm along the x direction. Only the beams among the electron beams emitted from the respective emitters that have passed through the small apertures of the multi-aperture plate 2 can enter said lens. Specifically, the multi-beam can be formed from the primary electrons. The same lens converges the multi-beam along the trajectories 3 onto the wafer 4. The electron beam apparatus carries out the evaluation of the sample by detecting the secondary electrons with the PMT 7 while moving the sample table with the sample 4 loaded thereon continuously in the y direction.

The front view of FIG. 1(a) shows an electric field E being applied in the direct current from the front surface to the back surface of the sheet, which serves to direct the secondary electron beam toward the FOP 6 is. Simultaneously with this, a deflecting electric field $\Delta E$ serving for providing the x-directional scanning with the primary electron beam is applied in the x direction. It is to be noted in this regard that taking the rotation induced by the magnetic field into account, the deflecting electric field $\Delta E$ is applied in the direction slightly rotated in the x direction.

To understand clearly an effect of the electric field E, looking at the electron beam apparatus of the present embodiment from the side, it can be recognized that the primary electron beam is deflected slightly toward the right due to the electric field E and converged onto the wafer 4, as shown in FIG. 1(b). Further, the secondary electrons emanating from the wafer 4 once form a crossover, as its trajectories are indicated by 5, and are focused into an image on the scintillator applied over the FOP (Fiber Optical Plate) 6 in its side facing to the vacuum side. In this connection, the rightward deflection of the secondary electrons by the electric field E permits the secondary electrons to be collected onto the scintillator surface distant from the electron source. An electron signal in the focused image is converted by the scintillator to an optical signal and transmitted via the FOP to the atmosphere, where it is detected by the PMT 7 and converted to an electric signal.

Looking at the electron beam apparatus of the present embodiment from the PMT side, it can been seen that in association with the deflection of the primary electron beam caused by the deflecting voltage $\Delta E$, the trajectories of the corresponding secondary electron beam varies as from the trajectories 5 to the trajectories 6a, as shown in FIG. 1(c).

The PMT 7 has a structure including a light-sensitive surface in a rectangular shape, as shown in FIG. 1(d).

Although the secondary electrons travels over a wider extent than the scanning width 9 of the primary beam, the detection should follow the direction at a certain angle from the x-axis as indicated by 7 in FIG. 1(d) because of the rotation induced by the magnetic field. Owing to this effect, the scanning can be carried out over an extensive range by the primary electron beams without overlapping of detection areas by respective beams.

It is also contemplated that instead of the PMT in itself including the rectangular light-sensitive surface, a light-sensitive surface 10 configured in a rectangular shape can be connected to an output surface 11 configured in a circular or other shapes and located in the PMT 12 side via a bundle of optical fibers provided as a photoconduction path, as shown in FIG. 1(e) (a second embodiment). Further, in case where the space between electron sources 1 is small and a large number of electron sources are to be arranged, the space between incident planes for the secondary electrons is also small and it would be occasionally difficult to arrange the optical fibers 10, 11 in place. In such a situation, the space between respective optical signals may be expanded by the optical lens and the optical fibers should be arranged on the light-sensitive surface, as shown by 10, 11, and thereafter the PMT 12 should be provided (a third embodiment).

Fourth to Eighth Embodiment

Figure 2:
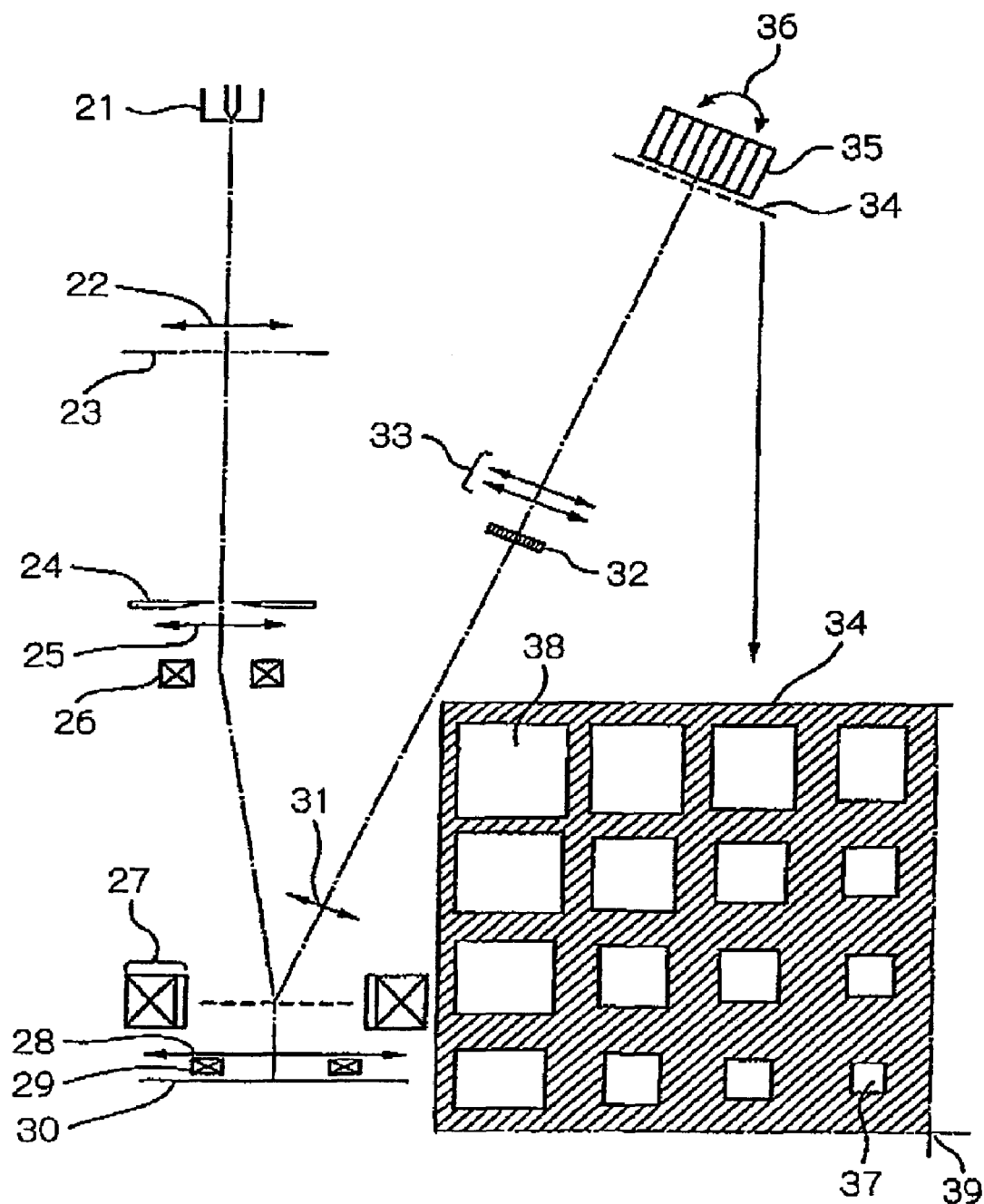
FIG. 2 is a schematic drawing depicting a configuration of an electron beam apparatus according to a fourth to an eighth embodiment of the present invention.

FIG. 2 shows schematically a configuration of an electron beam apparatus according to a fourth to an eighth embodiment of the present invention.

As shown in FIG. 2, the electron beam apparatus comprises an electron gun 21 of $LaB_6$ cathode for emitting a primary electron beam and a condenser lens 22 for converging the primary electron beam into a crossover in the vicinity of an NA aperture plate 24. A multi-aperture plate 23 having a plurality of apertures in the array of 8-row times 8-column is disposed below the condenser lens 22. The primary electron beam emitted from the electron gun 21 passes through the multi-aperture to be formed into a plurality of primary electron beams or the multi-beam. An reduction lens 25 and an objective lens 28 are disposed below the NA aperture plate 24. Respective beams of the multi-beam are reduced by two stages, one stage by the reduction lens 25 and the other stage by the objective lens 28, into individually narrowly converged irradiation spots on a sample 30, such as a wafer.

The electron beam apparatus further comprises a deflector 26 for making axial alignment and a beam separator 27. The beam separator comprises an electrostatic deflector and an electromagnetic deflector, which will be described later in detail, and they are set such that a force exerting from a magnetic field B on the primary electron beam should be as two times strong as the force exerting from an electric field E thereon so as to deflect the primary electron beam incident on the beam separator at a certain angle to be irradiated on the sample 30 substantially at a right angle, as will also be described later in more detail. On the other hand, the beam separator 27 is operable to deflect the secondary electrons incident on the beam separator from the sample side to the predetermined direction with respect to an optical axis thereof and thereby to separate the secondary electrons from the primary electron beam.

In this connection, the optical axis defined from the electron gun 21 to the deflector 26 and the optical axis of the objective lens 28 and of the beam separator 27 are offset from each other in the x y directions by about 20 mm (a fourth embodiment). A chromatic aberration from the deflection can be eliminated almost completely by setting the deflection by the electromagnetic deflector of the beam separator 27 as approximately two times strong as the deflection by the electrostatic deflector of the beam separator 27 (the term "approximately" is used herein in consideration of the contribution from the axial aligning deflector 26). As a result, there should be no problem from the viewpoint of the aberration, even if the beam separator is not disposed on a conjugate plane with the sample 30. Only a magnetic deflector is also useful for the beam separator.

Further, to meet the condition where the sample 30 are scanned with a multiple of irradiation spots on the surface thereof, a deflector is provided, which is operable to vary a deflection voltage so as to deflect the primary multi-beam in the x direction. Such a deflector usable for the scanning control may include, for example, the axial aligning deflector 26 and the electrostatic deflector of the beam separator, which may also serve as the scanning deflector.

Along the direction of the secondary electron beam deflected by the beam separator 27, disposed are, respectively, a magnifying lens 31, a FOP 32 comprising a bundle of optical fibers with a scintillator applied on the front surface thereof for converting an electron beam to light, an optical zoom lens 33, a multi-aperture plate 34 including a plurality of apertures in the array of 8-row times 8-column formed therethrough, a PMT array 35 for detecting intensity of the light transmitted through each aperture of the multi-aperture, and a rotation mechanism capable of adjusting a rotational position of the PMT array around the optical axis.

Further, the multi-aperture plate 34 is configured such as shown in the lower section of FIG. 2 that the apertures located closet to the optical axis 30 (e.g., aperture 37) have the aperture areas that are smaller than those of the apertures located farther from the optical axis (e.g., aperture 38). A deflector (not shown) for deflecting the secondary electron beam in synchronization with the deflecting motion of the multi-beam of the primary electrons is operatively arranged in the step subsequent to the magnifying lens 31 so as to direct each beam of the multi-beam of the secondary electrons through each corresponding aperture of the multi-aperture plate 34 even under the scanning that is carried on over the sample with the irradiation spots.

The PMT array 35 is connected with an image processing unit, though not shown, via an A/D converter. The image processing unit forms and outputs an image of the sample 30 based on the light intensity distribution that has been detected by the PMT array 35. Further, the output image signals are sent to a CPU (not shown) serving for controlling and managing respective components of the electron beam apparatus, where an evaluation including a defect detection of the sample 30 based on the image may be carried out. It is to be noted that the sample 30 has been placed on a stage, though not shown. The stage is controlled in accordance with instructions from the CPU so that the stage may be moved continuously in the y direction at a right angle relative to the x-direction or the direction of scanning, and that the stage may be moved in a step-by-step manner upon changing scanning stripes.

An operation of the first embodiment will now be described.

The primary electron beam emitted from the electron gun 21 is converged by the condenser lens 22 and passed through the plurality of apertures of the multi-aperture plate 23 to be shaped into the multi-beam in the array of 8×8 and to form the crossover in the vicinity of the NA aperture 24. The multi-beam of the primary electrons is reduced by the reduction lens 25 and deflected by the axial aligning deflector 26 to pass through the axially offset beam separator 27, and the multi-beam after exiting from the beam separator 27 is again reduced by the objective lens 28 into the image on the sample 30. Simultaneously, the multi-beam is deflected so that the scanning can be carried out with the spots moving over the sample in a certain direction (e.g., in the x direction). Those secondary electrons emanating from the scanned points are deflected toward the right on the drawing sheet, when transmitted through the beam separator 27, to enter the magnifying lens 31, where the space between respective groups of secondary electrons in the form of multi-beam is extended, and the secondary electrons activate the scintillator applied on the front surface of the FOP 32 to emit light. Since the FOP 32 is made of optical fibers, each having a self-focusing function, or material having a high refractive index in the central region and a low refractive index in the peripheral region, therefore the optical signals entered at different incident angles are to come out with their angles relative to the optical axis having been reduced at the exit of the FOP 32. Accordingly, even with a larger F number of the optical zoom lens 33 in the subsequent step, the light having exited from the FOP 32 can enter the lens 33 efficiently. Owing to the configuration that the lens 33 is implemented as the zoom lens, even if the space between respective beams of the multi-beam of secondary electrons dependent on the resultant magnification scale from the objective lens 28, the magnifying lens 31 and others is different from the design value, simply changing the magnification scale (focal distance) of the zoom lens 33 can provide the match between the beam space and the pitch of the PMT array 35 easily (a fifth embodiment). In addition to the above advantage, to modify the beam space in the primary multi-beam in order to change a pixel size, as well, simply changing the magnification of the zoom lens 33 can provide the match between the beam space and the pitch of the PMT array 35 easily. Still advantageously, even if the orientation of the array of the secondary electron images is offset from the orientation of the PMT array 35 due to the different rotational amount of the electromagnetic lens 31 from the design value, the rotation mechanism 36 (a sixth embodiment) can help adjust the rotational position of the PTM array to thereby achieve the match in orientation easily. It is to be noted that the fifth and the sixth embodiments are applicable not only to the electron beam apparatus performing the scanning operation with the multi-beam but also that with a single beam.

Further, since the multi-aperture plate 34 including the aperture 37 having a smaller area adjacent to the optical axis 39 and the aperture 38 having a larger area distant from the optical axis is disposed in front of the PMT array 35, it can help compensate for the deteriorated secondary electron signal intensity in conjunction with the deteriorated off-axis intensity of the electron gun 21 and/or the deteriorated signal of the secondary electron enlarged image due to the aberration from the secondary optical system (a seventh embodiment). It is also useful that only peripheral apertures have rectangular shapes with a larger side.

Figure 3:
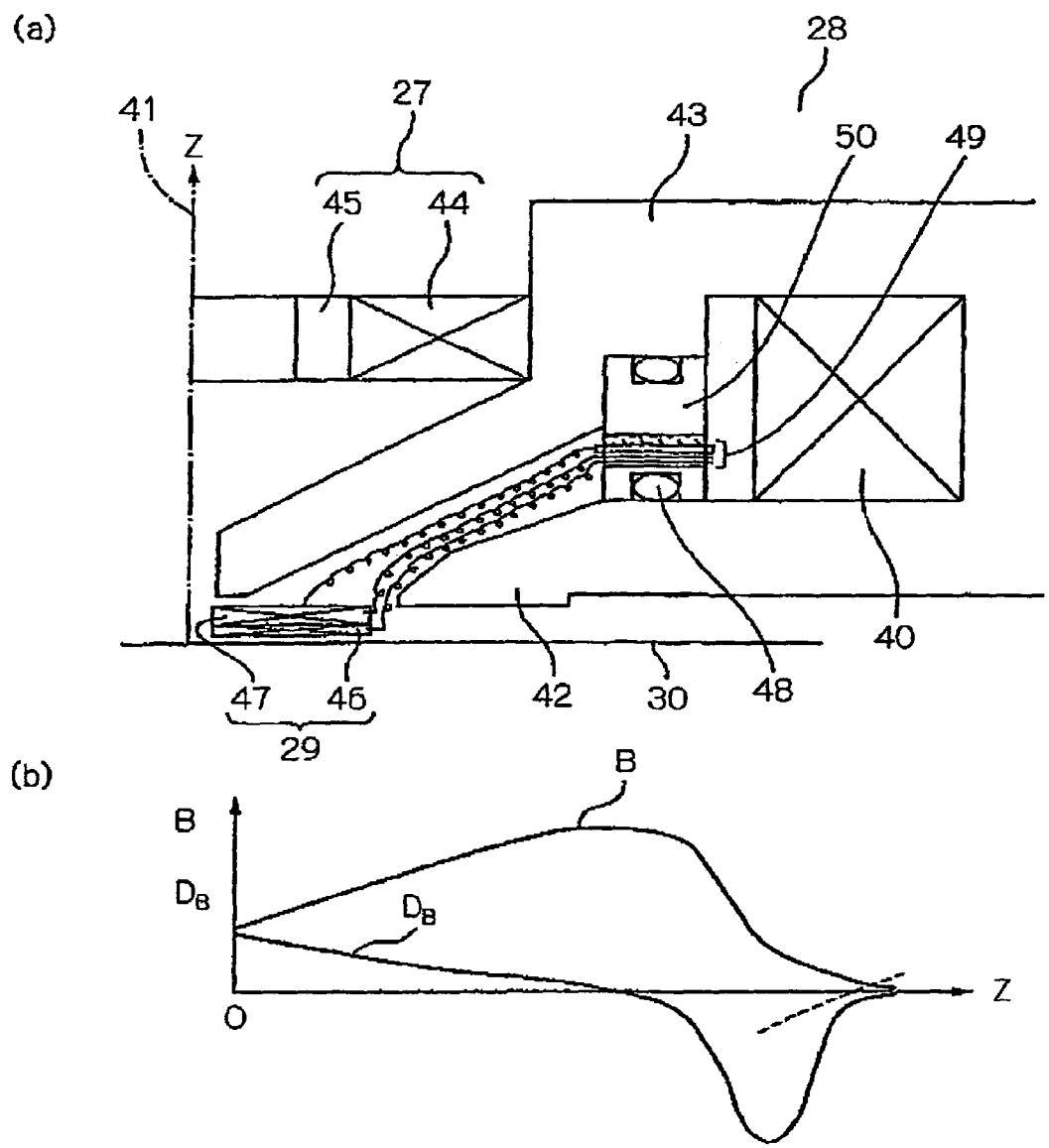
FIG. 3(a) shows a detailed configuration of an objective lens of the electron beam apparatus of FIG. 2 (the eighth embodiment)
FIG. 3(b) is a graphical representation indicating an axial magnetic field distribution for the objective lens of FIG. 3(a)

FIG. 3(a) shows a detailed configuration of the objective lens 28 of the electron beam apparatus of FIG. 2 as an eighth embodiment. As shown in FIG. 3(a), the objective lens 28 has a structure including a magnetic excitation coil 40 inside an inner magnetic pole 43 and an outer magnetic pole 42 with lens gap defined in the sample 30 side. An electromagnetic deflector 29 comprising two pairs of electromagnetic deflection coils 47, 46 is disposed between the lens and the sample 30. The coil current from those pairs of coils is taken out through the hermetic seal 49 into the atmosphere side. The exciting coil 40 is isolated from the vacuum zoon by a seal cylinder 50 sealed with an O-ring 48. The beam separator 27 comprises an electrostatic deflector 45 and an electromagnetic deflector 44, whose core is shared with an inner surface of the inner magnetic pole 43.

An axial magnetic field distribution of the objective lens 28 is indicated in a graphical representation of FIG. 3(b). Further, the differentiation of the magnetic field B with respect to the optical direction, z, is indicated by $D_B$. The MOL (Moving Objective Lens) motion can be generated by bringing the z-dependency of the deflecting field by the electromagnetic deflector 29 close to the distribution of $D_B$. The z-dependency of the deflecting magnetic field by the electromagnetic deflector 29 can be brought close to the $D_B$ by making the coil 47 and the coil 46 produce their magnetic fields in opposite directions from each other and by adjusting the relative intensity thereof to each other. It is to be noted that a bobbin for the coil may be made of ceramics with metal coating applied to its outer surface, to which a positive voltage may be applied, to thereby construct an axisymmetric electrode.

The aberration resultant from the primary and the secondary multi-beam entering the locations off from the optical axis of the objective lens 28 during the scanning operation can be reduced by moving the optical axis of the objective lens 28 electro-magnetically by the MOL motion performed in synchronization with the scanning operation. This prevents deterioration of the resolution even during the scanning operation with the multi-beam on the locations distant from the optical axis, and further advantageously this ensures that each beam of the multi-beam can be detected by the PMT array 35.

Although the scanning operation with the multi-beam has been described with reference to the eighth embodiment, the present invention is not limited to the above illustrated example but may be applicable to the case where the MOL motion is performed in an electron beam apparatus, in which a sample is scanned with a single beam and then secondary electrons or the like emanating from the scanned surface are map-projected onto a detection surface by means of an image projection optical system.

Ninth Embodiment

Figure 4:
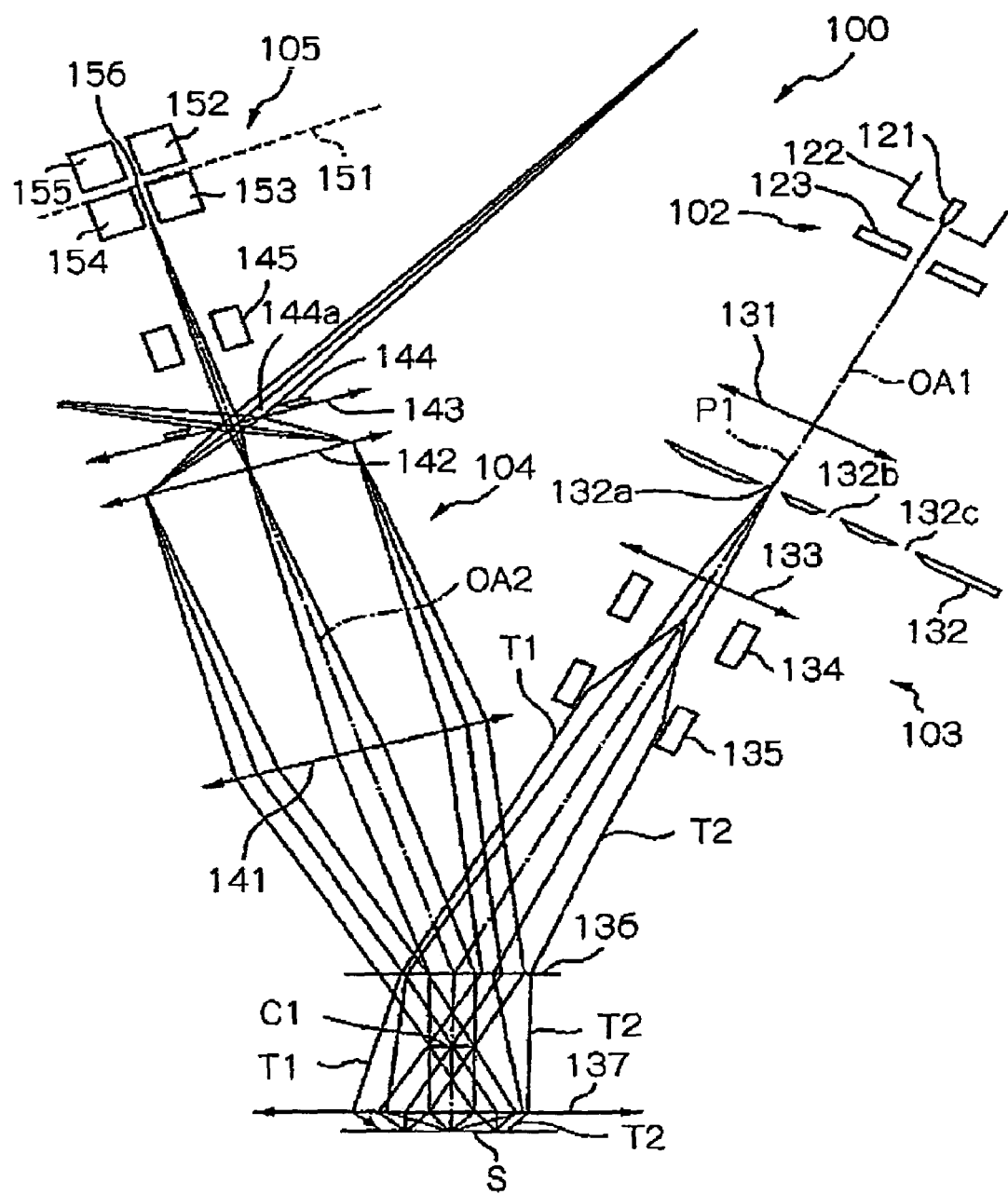
FIG. 4 is a schematic drawing depicting a configuration of an electron beam apparatus according to a ninth embodiment of the present invention.

FIG. 4 shows an electron beam apparatus according to a ninth embodiment of the present invention. An electron beam apparatus 100 comprises an electron gun 102 provided as a unit for generating an electron beam, a primary electron optical system (hereinafter simply referred to as a primary optical system) 103 for guiding the electron beam emitted from the electron gun 102 to a surface of a sample S, a secondary electron optical system (hereinafter simply referred to as a secondary optical system) 104 for guiding secondary electrons emanating from the surface of the sample (hereinafter referred to as the sample surface) by the irradiation of the electron beam to a detector, and a detection system 105.

The electron gun 102 comprises a cathode 121, a Wehnelt 122 and an anode 123 and is operable under the space-charge limited condition to emit an electron beam with a small shoot noise. The cathode 121 is assuming a part of a sphere having a radius of curvature of about 100 μm in a tip portion thereof and if applied with an electron gun current not lower than 1 mA, the cathode 121 is able to emit the electron beam having a high intensity and a high emittance.

The primary optical system 103 comprises a condenser lens 131, an aperture plate 132 including a shaping aperture 132a formed therethrough, a condenser lens 133, a sub-field selecting deflector 134, 135, a beam separator 136 and an objective lens 137, which are disposed in this sequence along an optical axis OA1 from the electron gun 102 side, as shown in FIG. 4. The aperture plate 132 further includes other shaping apertures 132b for replacement and 132c that is differently sized, both of which are offset from the shaping aperture 132a. The shaping aperture 132b for replacement has been provided for the replacement for the original shaping aperture 132a in case of its having become contaminated. The differently sized shaping aperture 132c is to be used to change an area of irradiation range of the electron beam. The switching among those shaping apertures can take place by shifting the aperture plate 132 in the direction normal to the optical axis OA1 and parallel to the sheet of FIG. 4 so that either one of those apertures can be selected. Although FIG. 4 shows the arrangement in which the shaping apertures are linearly oriented in the vertical direction to the optical axis OA1 by one for respective types of aperture, a plurality of shaping apertures (the differently sized shaping apertures may be sized differently from each other) may be arranged along the direction normal to the sheet of FIG. 4, and in that case the aperture plate 132 may be moved in the direction normal to the optical axis OA1 and parallel or normal to the sheet of FIG. 4 by means of an external device such as a bellows so as to select either one of the apertures for use.

Further, the secondary optical system 104 comprises a magnifying lens 141, an auxiliary lens 142, a magnifying is lens 143, an NA aperture member 144 for defining an NA aperture 144a, and a deflector 145, which are positioned in this sequence along an optical axis OA2 from the sample S side, as illustrated.

Reference numeral 151 designates a scintillator surface of the detection system 105 and the scintillator surface 151 are segmented into a plurality of areas, each of them defining a light-sensitive surface. They are illustrated as four light-sensitive surfaces 152 to 155 in the present embodiment. It is to be noted that although the four light-sensitive surfaces are illustrated side-by-side in a plane of the sheet of FIG. 4, this part is herein particularly showed in a plan view looked along the optical axis for the purpose of clear illustration. That is, the four light-sensitive surfaces are actually positioned on the scintillator surface with a center point of their arrangement 156 placed on the optical axis OA2.

Figure 5:
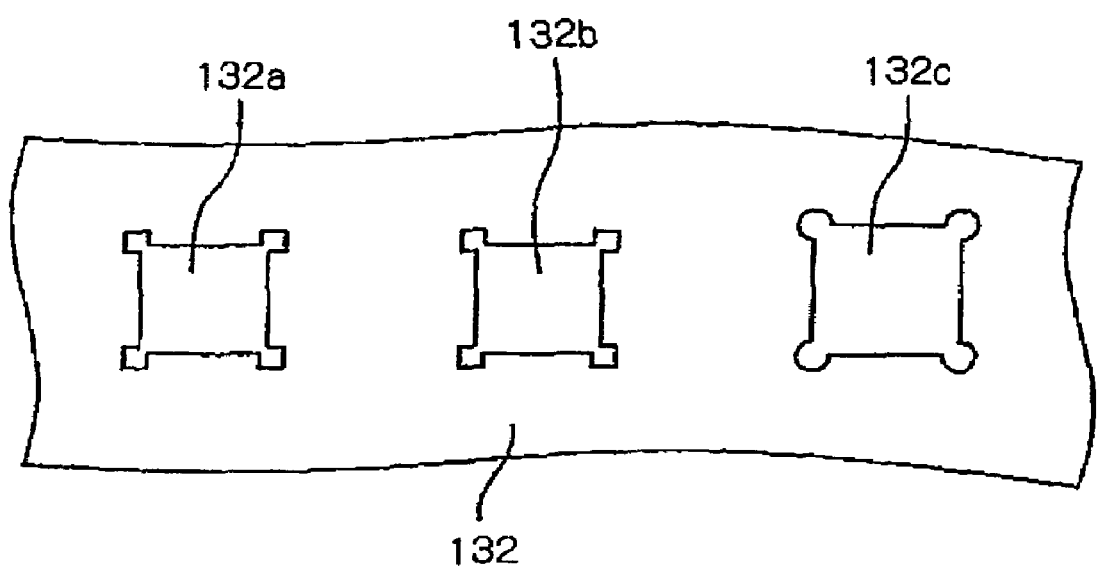
FIG. 5 is an enlarged plan view of an aperture plate used in the electron beam apparatus of FIG. 4.

In the electron beam apparatus 1 having the above-described configuration, the electron beam emitted from the electron gun 102 is condensed by the condenser lens 131 into a crossover formed at a point P1. The electron ray or the electron beam diverging from the crossover is formed into a square shape by the shaping aperture 132a and reduced by the condenser lens 133 and the objective lens 137 into a projected image on the surface of the sample S. Each of the shaping apertures 132a, 132b and 132c includes auxiliary apertures at four corners of its square aperture as shown in FIG. 5 so as to prevent the beam current density from decreasing at four corners due to the aberration. The shape of the auxiliary aperture may be in any shape that is effective to prevent the decrease in beam current density. To increase or decrease the beam current, the current to be applied to the electron gun may be changed, and thereby the intensity of the electron beam can be changed over an extensive range.

It is to be noted that in the present embodiment, the field of view is segmented into a plurality of sub-fields and the image formation is performed in units of sub-field.

It is possible to adjust the condenser lens 131 so that a conjugate point by the condenser lens 133 for the crossover at the point P1 may be on the principal plane of the objective lens 137. The irradiation condition for the primary beam is controlled such that the primary beam is not vertically incident upon the sample surface at a right angle but it should be Incident upon the sample surface from the left side farther away from the optical axis OA1 of FIG. 4, as indicated by the trajectories T1 when irradiating the sub-field on the left side with respect to the optical axis OA1, and that it should be incident upon the sample surface from the right side farther away from the optical axis OA1, as indicated by the trajectories T2 when irradiating the sub-field on the right side with respect to the optical axis OA1. By setting the incident condition as described above, reflected electrons that are generated secondarily or secondary electrons would not follow the simple cosine law but exhibit the beam intensity distribution characterized by an emission angle that inclines toward the optical axis side with respect to the principal ray, meaning that the beam can enter the objective lens at a point closer to the optical axis and thus the aberration can be reduced.

The secondary electrons emanating from the sample surface are transmitted through a doublet lens consisting of the objective lens 137 and the magnifying lens 141, which produces the magnified image of the secondary electrons on the auxiliary lens 142 placed in the next stage in the downstream side (along the advancing direction of the secondary electrons). In this connection, an absolute value of the integrated value of the axial magnetic field produced by the objective lens 137 from the sample surface has been set to be equal to that of the magnifying lens 141. Further, if the distance determined by multiplying the distance between the objective lens 137 and the crossover image CI of the sample by the magnification scale of the image is set to meet the condition that it is substantially equal to the distance between the crossover image CI and the magnifying lens 141, the chromatic aberration from the magnification scale and rotation and the distortion aberration could be minimized. The lens 141 in the upper side of the doublet lens has a longer focal length than the lens 137 in the lower side of the doublet lens but has the substantially same AT number with that, and thus the long focal length can be obtained by making the lens gap larger.

Since the image of the sample S on the auxiliary lens 142 comes out in the magnification scale on the order of 10, therefore the field of view has been extended by about 10 times. Accordingly, if no auxiliary lens 142 is provided, since the principal ray incident upon the magnifying lens 143, particularly the ray from the image distant from the optical axis is advanced in parallel to the optical axis, it enters the magnifying lens 143 at the point away from the optical axis, and thereby produce a significant aberration. However, owing to the small aperture angle, there should be no problem of the aperture aberration but the distortion aberration and the transverse chromatic aberration should be seriously problematic. If taking advantage of the auxiliary lens 142 and determining the condition of the auxiliary lens 142 such that all of the principal rays can gather in the vicinity of the principal plane of the magnifying lens 143, then those types of aberration could be reduced to be negligibly small. The simulation result shows that the aberration has been observed much smaller in the case of the point offset from the principal plane of the magnifying lens 143 toward the scintillator surface 151 side by 2 mm to 3 mm.

The scintillator surface 151 is segmented into the four virtual areas 152, 153, 154 and 155 as the light-sensitive surfaces, and the image thereof is focused on the CCD via an optical lens (not shown) placed in the subsequent step (above the scintillator in FIG. 4). It is to be noted that the CCD also includes a plurality (four in the present invention) of surfaces capable of projecting the two-dimensional image in consistency with the plurality (four in the present embodiment) of light-sensitive surfaces. The exposure time of the CCD is as short as 5 µs but reading of the data takes 10 µs or more, and so when a single CCD is used to take an image, in spite of the short exposure time of 5 µs, the CCD has to wait for 10 µs after one exposure for starting another exposure. To address this drawback, the present embodiment has prepared four light-sensitive surface as shown in FIG. 4, wherein when the exposure has been completed on one of the light-sensitive surfaces (e.g., the area 152), the deflector 145 deflects the electron image to be transferred onto an adjacently located second light-sensitive surface (e.g., the area 153) and the subsequent sub-field is irradiated thereon. Thus, during the exposure being carried out on a third light-sensitive surface (e.g., the area 154), the data from the image on the first light-sensitive surface (e.g., the area 152) can be forwarded, then the image could be serially formed with only a loss time defined by the settling time of the deflector. It is to be noted that the settling time used herein implies the time required in controlling the physical quantity of the subject from an initial value to a target value, specifically the time consumed from the input of a control signal until the physical quantity has fallen in a range of target value ±allowance.

From the fact that the same NA aperture 144a is used for the image formation from both of sub-field closer to the optical axis and sub-field distant from the optical axis, it should be apparent that the sub-field distant from the optical axis is associated with more significant aberration and fewer number of electrons entering in a normal pixel. To compensate for that, in the present embodiment, the irradiation time is controlled dynamically to be variable so that the irradiation time of the electron beam and thus the image formation time in the CCD for the sub-field distant from the optical axis can be set longer than for the sub-field closer to the optical axis, to thereby produce the substantially same level of S/N ratio over the entire field of view.

Tenth Embodiment

Figure 6:
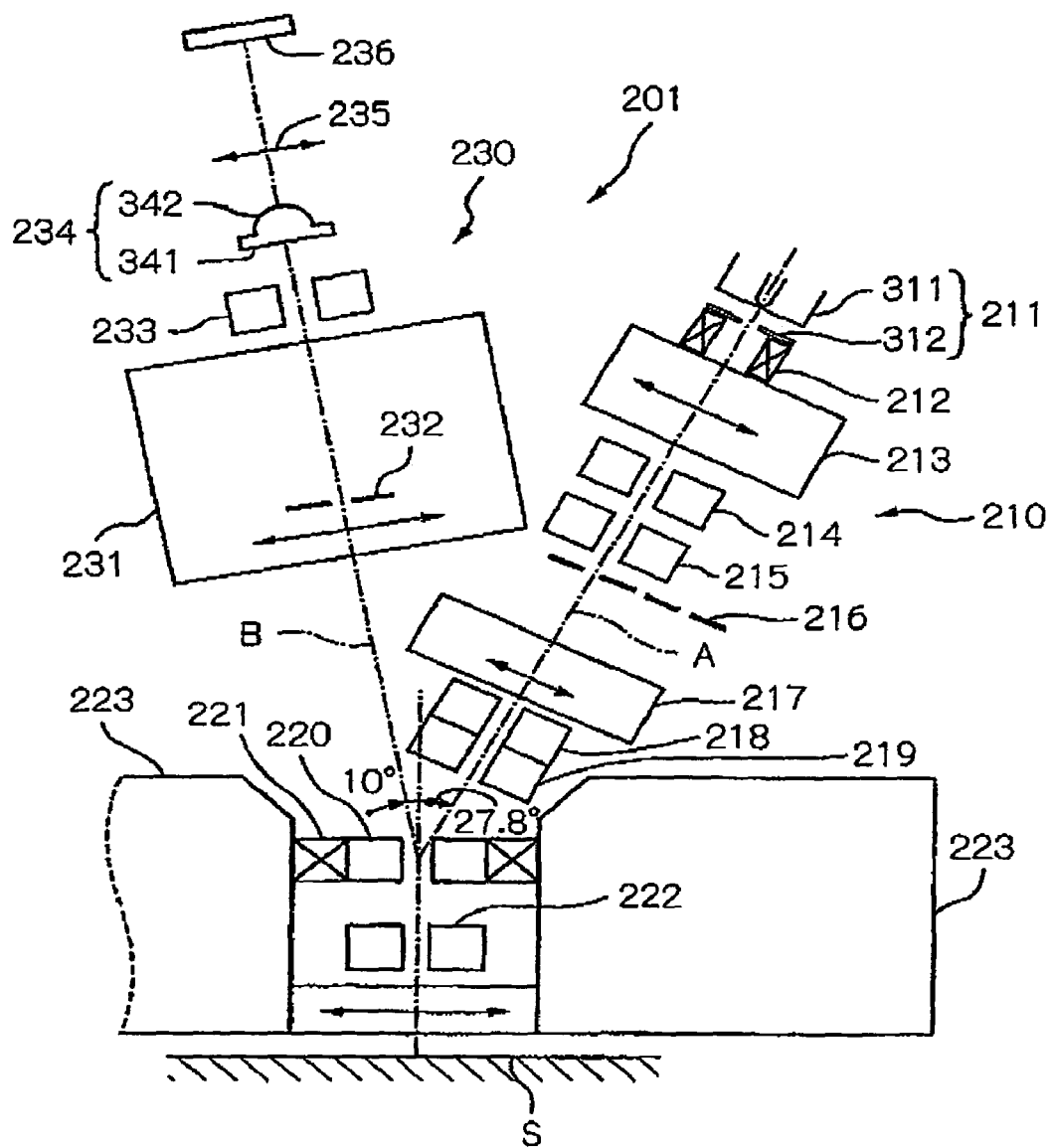
FIG. 6 is a schematic drawing depicting a configuration of an electron beam apparatus according to a tenth embodiment of the present invention.

FIG. 6 shows schematically an electron beam apparatus 201 according to a tenth embodiment of the present invention, this electron beam apparatus comprises an irradiation optical system 210 in which an electron beam emitted from an electron gun is shaped into a predetermined configuration (e.g., a plurality of beams or a rectangular shape of beam) and thus shaped beam is irradiated onto a surface of a sample S (e.g., a wafer) to be inspected, and an image projection optical system 230 for focusing secondary electrons emanating from the sample S into an image on a detector.

The irradiation optical system 210 comprises an electron gun 211 including a thermionic emission cathode (LaB$_6$ cathode) 311 and an anode 312 and operable to emit an electron beam in a spatially restricted area, an axial aligning deflector 212, a lens 213, a deflector 214 to be superimposed with a blanking signal for blanking the electron beam for a period requiring no electron beam irradiation, a deflector 215 operable associatively with the deflector 214 to perform an axial aligning operation, a shaping aperture 216 for shaping the electron beam into an electron beam having a desired cross section, a lens 217, and a deflector 218, 219 operable to select a sub-field and having a function to control the electron beam so as to run along its trajectories a certain distance apart from the trajectories of the secondary electrons, all of which are disposed in this sequence with the electron gun 211 on the top along an optical axis A defined at a certain angle relative to a direction normal to the surface of the sample S, as shown in FIG. 6. The irradiation optical system 210 further comprises a beam separator (220, 221) for deflecting the electron beam with the aid of a field where an electric field and a magnetic field are crossed at a right angle and also for separating secondary electrons from the sample S, a deflector 222 and an objective lens. 223, all of which are disposed along an optical axis C following the direction normal to the surface of the sample S.

Figure 7:
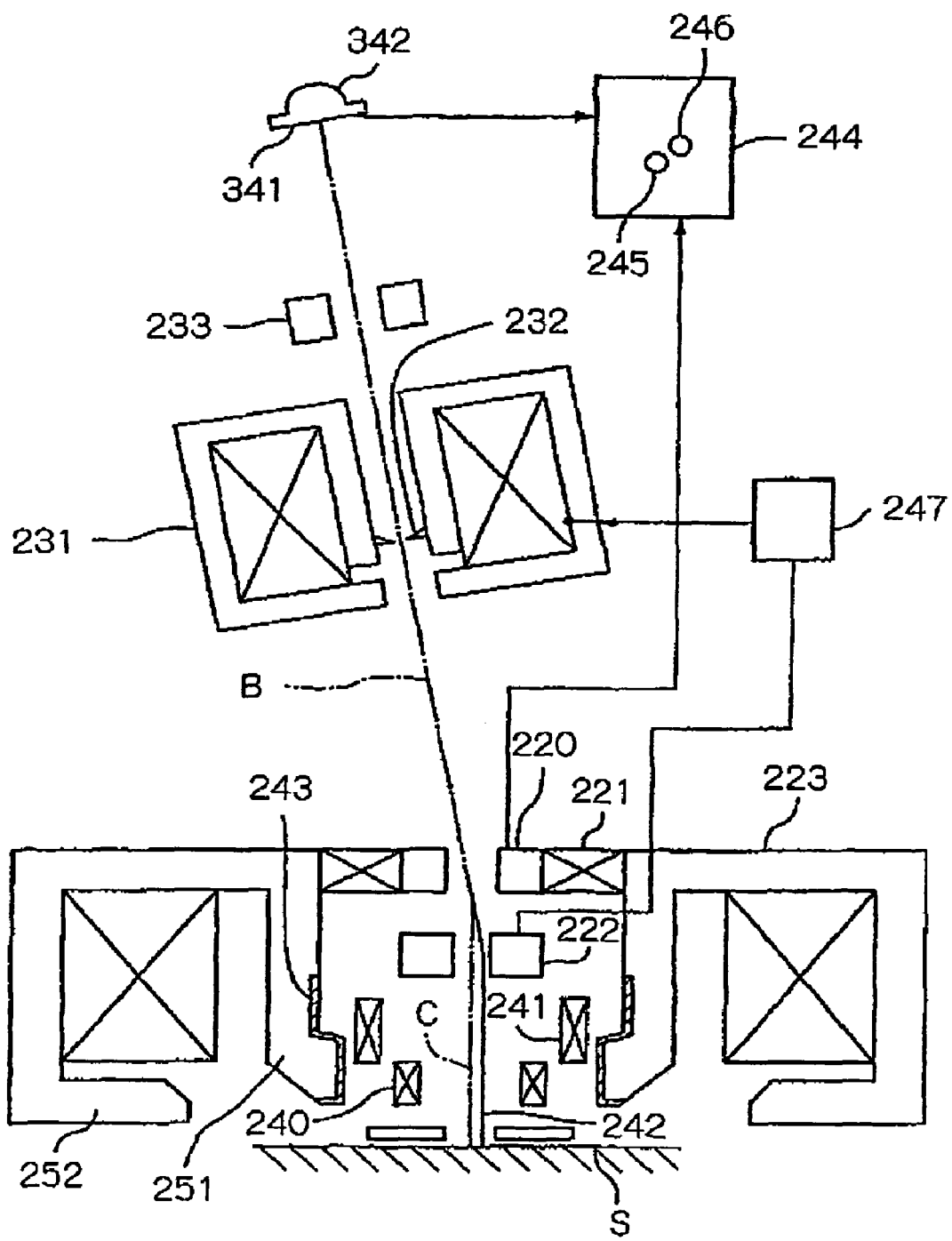
FIG. 7 is an illustration showing schematically an electron beam transfer unit using an optical system of an electron beam apparatus according to an eleventh embodiment of the present invention.

The beam separator (220, 221) is composed of an electrostatic deflector 220 and an electromagnetic deflector 221. Further, the objective lens 223 is incorporated with the beam separator (220, 221) and a deflector 222 and further provided with a magnetic lens including a magnetic gap defined by an inner magnetic pole 251 and an outer magnetic pole 252 in the sample side (FIG. 7).

The image projection optical system 230 is disposed along an optical axis B of the image projection optical system in the direction at a certain angle with the surface of the sample S, and comprises a magnifying lens 231 for magnifying secondary electrons, an NA aperture 232, a deflector 233 for selecting a CCD detector, an optical member 234, an optical lens 235 and a CCD detector 236. The NA aperture 232 is incorporated inside the magnifying lens 231.

In the above configuration, the electron gun 211 forms a crossover image between the cathode 311 and the anode 312. The crossover image is gradually converged by the lenses 213 and 217 into an image on a principal plane of the objective lens 223. Simultaneously with this, the electron beam emitted from the electron gun 211 is converged by a small amount by the lens 213 to irradiate the shaping aperture 216, where the electron beam is shaped in the form of electron beam and forms an image of the shaping aperture. If the beam diverging from the NA aperture has a larger light flux on the lens 217 than on the objective lens, the crossover image may be formed on the principal plane of the lens 217. The image of this shaping aperture is gradually converged by the lens 217 and the objective lens 223 to enter the beam separator (220, 221), where it is deflected into the direction normal to the surface of the sample S to form the image of the shaping aperture on the sample S. The beam separator (220, 221) has a function for directing the electron beam by deflecting its course by an angle of 27.8 degrees toward the normal line of the sample S and another function for directing the secondary electrons to opposite direction by deflecting their course by an angle of 10 degrees.

Since the system employs the two-stage type of lens for both of the crossover image and the image of the shaping aperture to be converged gradually, meaning that no image is formed between the lenses in the two-stage arrangement and the image of the shaping aperture is produced on the sample surface while satisfying the Koehler's illumination condition, therefore there is no need to significantly intensify the excitation level of each lens, and so the lens can be sized smaller and further the optical path for the irradiation optical system can be made shorter.

The secondary electrons emanating from the sample S by the irradiation of the electron beam are converged by the objective lens 23, deflected by the beam separator (220, 221) along the optical axis B, and focused into a magnified image in front of a lens 231 of the image projection optical system 230. This magnified image is further magnified by the magnifying lens 231 and formed into an image on a surface 341 of an optical member 234 applied with the scintillation thereon. The image is further magnified by an optical lens 235 into an image on a CCD detector 236 having a pixel size of 10 some microns.

As discussed above, since the image projection optical system of the electron beam apparatus of the present invention needs no MCP or FOP, and the electron optical system is only required to form a magnified image in the magnification scale on the order of 100, meaning that only the magnification scale of 10 is required respectively for the magnifying lens 231 and the optical lens 235 in the two-stage of lens, therefore the optical path length of the image projection optical system can be reduced to about 200 mm. Advantageously, this can help reduce the blur of the electron beam from the space charge effect.

Figure 8:
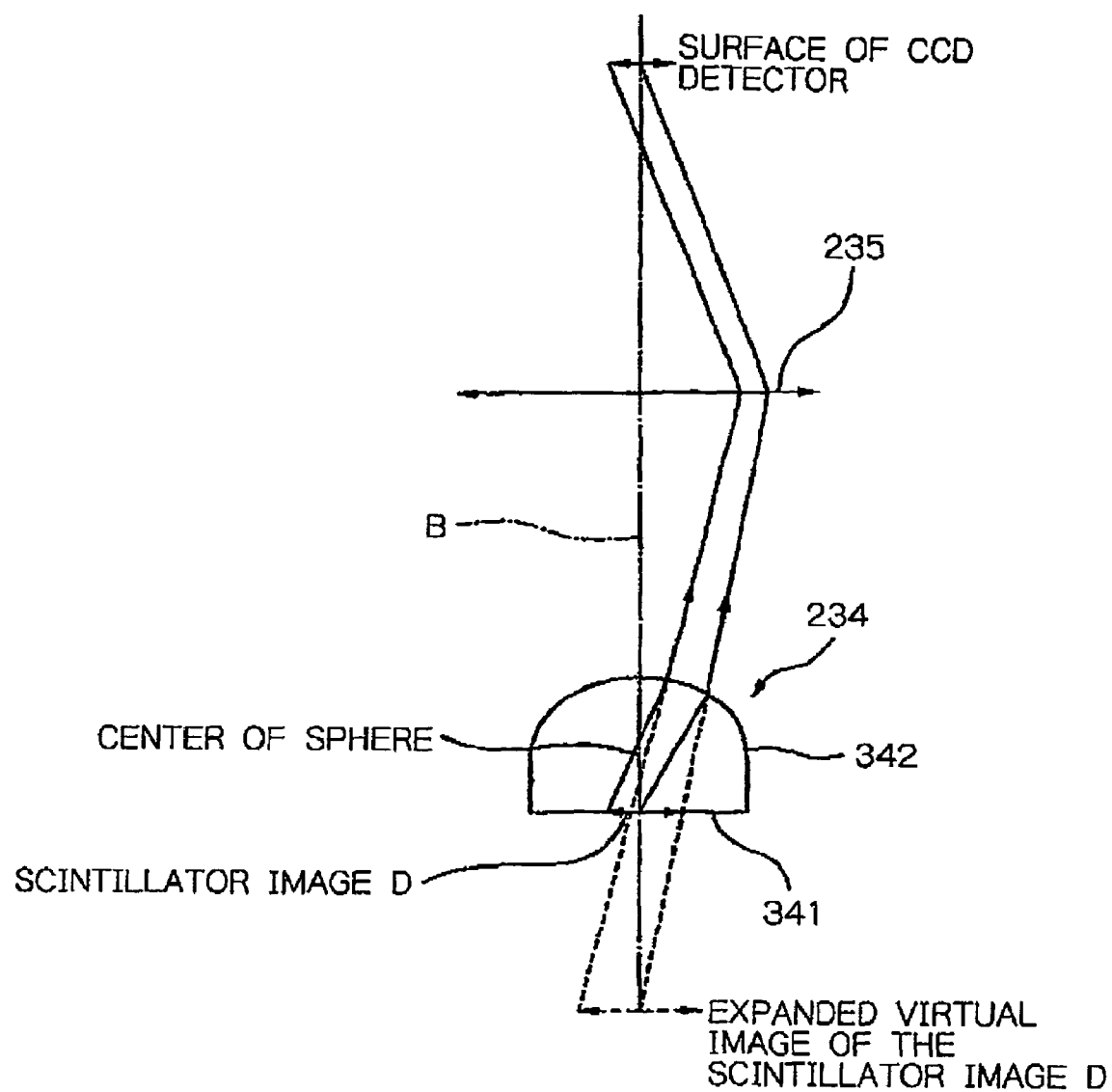
FIG. 8 shows how the optical member illustrated in FIG. 7 operates to project a scintillator image in a magnified scale on a CCD detector.

The optical member 234 includes the one surface 341 facing to the sample side, which is defined in the vacuum side, and has been polished to a flat surface and applied with the scintillator. The other surface 342 facing to the optical lens side is defined in the atmosphere side, and has been polished to assume a semi-spherical shape having a center on said flat surface. Accordingly, this optical member 234 constructs an immersion lens. The reason why the other surface has been made in the semi-spherical shape comes from the fact that if the other surface was a flat surface, when the optical signal generated in the scintillator goes out of the optical member into the atmosphere, it could be bent outward with respect to the optical axis B of the image projection optical system due to a refraction angle, and accordingly the lens having a small f/number (i.e., clear) is necessary in order to receive the optical signal effectively in the optical lens 235, whereas if the other surface is made in the semi-spherical shape, the optical signal originating from the center makes an angle proximal to the parallel relationship with the optical axis, so that the optical lens 235 having a relatively large f/number is still usable to focus the majority of optical signals into the image on the CCD detector 236. The semi-spherical surface 342 may define a hyper semi-spherical surface having the center offset to the optical lens side from the flat surface 341. In that case, the transmission of light should be further improved. Further, if such an optical member is provided to pass through, the image aberration may be induced in an image in a position away from the optical axis due to the spherical aberration, and accordingly, the surface 342 may be non-spherical surface, such as paraboloid of revolution, for example. Further, since the scintillator image D appears to be expanded, as shown in FIG. 8 in detail, the lens of lower resolution is still able to form the image without any lack of a fine pattern of MTF. In either case, if the radius of curvature of the semi-spherical surface 342 to the size of the image is made larger sufficiently, the aberration could be reduced to a negligible level. Further, the aberration generated from this spherical member can be corrected by the lens in the subsequent stage. Such a relay optical system needs no MCP or FOP, and favorably the maintenance work for the optical system can be made easier.

The deflector 233 is provided for the purpose that the image otherwise to be formed on the optical axis B may be deflected to be formed on image planes of the CCD detectors 236 positioned at four different locations, sequentially, to thereby help reduce a long image-reading time of the CCD detector.

In FIG. 6, a plurality of apertures may be formed in the shaping aperture 216, and in that case, the plurality of apertures are to be irradiated with the electron beam with an uniform intensity to shape the electron beams, which are in turn used by the deflector 218, 219 to irradiate the sample surface S, and then the secondary electrons emanating from the sample are focused by the image projection optical system 230 into the image on the scintillator 341 and finally the optical signal may be taken out of the curved surface 342.

Eleventh Embodiment

FIG. 7 is a diagram for illustrating a method for reducing the aberration and an optical axis adjusting method in the image projection optical system 230 of the electron beam apparatus of the present invention, showing an internal configuration of the objective lens 223 and the magnifying lens 231 of FIG. 6. The optical lens and the CCD detector are herein omitted.

There has been a known technology in the lithography and the like that a shaped beam on an optical axis is deflected by a deflector into an image on a sample at a point away from the optical axis, while at the same time, an objective lens is driven to perform the MOL motion to thereby reduce the aberration. In the present invention, in contrast to the above discussed lithography process, the secondary electrons on an object point distant from an optical axis C are processed through the MOL motion to reduce the aberration, and advanced along the optical axis B by the two-stage of deflectors 222, 220 to pass through the NA aperture 232.

In FIG. 7, a set of electromagnetic deflectors 240, 241 is disposed inside the objective lens 223 for performing the MOL motion. A differential value of an axial magnetic field distribution exhibits a sharp rise in the vicinity of the sample, which is gradually lowered toward the image side (see FIG. 3(b)). Accordingly, in the set of electromagnetic deflectors 240, 241 serving for producing a deflecting magnetic field, one electromagnetic deflector 240 for generating a deflection field having an intensity distribution of small half-value width has a small coil diameter, while the other electromagnetic deflector 241 for generating a deflection field having an intensity distribution of large half-value width has a larger coil diameter as well as a larger coil size in the z direction (along the height). With the deflector magnetic field distribution approximately matched to the differential value of the axial magnetic field distribution of the objective lens 223, trajectories 242 of a principal ray of secondary electrons follows the line offset from but approximately parallel to the optical axis C, and is deflected by the deflector 222 toward the optical axis B and crossed with the optical axis C at the location of the deflector 220 of the beam separator, which deflects the secondary electrons to be advanced on the optical axis B. In order to carry out the deflecting operation at high speed, a circular cylinder of ferrite 243 is provided on an inner wall of the internal magnetic pole of the objective lens 223.

There will now be described a method for adjusting the optical axis, while observing the actual secondary electrons, such that the principal ray having exited from the objective lens is transmitted through the center of said magnifying lens and also through said NA aperture. The condition for performing the MOL motion of the electromagnetic deflector 240, 241 may be determined through the simulation to find an optimal condition for the aberration. To direct the principal ray of the secondary electrons to pass through the lens center of the magnifying lens 231 and also through the center of the NA aperture 232, the deflector 220 of the beam separator is applied with the scanning current for providing the two-dimensional scanning in the x and y directions, and the current generated by the secondary electrons entering the scintillator on the flat surface 341 is applied to the intensity modulation input of a CRT monitor 244, which may then display such a bright aperture image as indicated by reference numeral 245 or 246 in the CRT monitor under the condition allowing the secondary electrons to be transmitted through the NA aperture 232. In this condition, if wobbler is applied by a controller 247 to the excitation of the magnifying lens 231 subject to the axial alignment, it can be observed that the bright aperture image like the one shown in the CRT monitor 244 is separated into two images (reference numeral 245 and 246). In this circumstance, if the two values, X and Y, of the deflector 222 are changed by the controller through trial and error, the condition required for the separated bright aperture images 245 and 246 to approach to each other into a substantially overlapped state can be found. This is the condition for adjusting the optical axial such that the principal ray having exited from the objective lens can be directed to pass through the center of said magnifying lens and also through said NA aperture. The deflector 220 used for the two-dimensional scanning in the x and y directions and the deflector 222 used for the trial and error attempt may be exchanged to each other.

Although the description has been made to the method for manually adjusting the optical axis while observing the CRT, alternatively a computer may be used to measure the bright region through a pattern recognition, and the operation may be automatically executed in accordance with the above-described procedure.

Eleventh Embodiment; Manufacturing Method of Semiconductor Device

Figure 9:
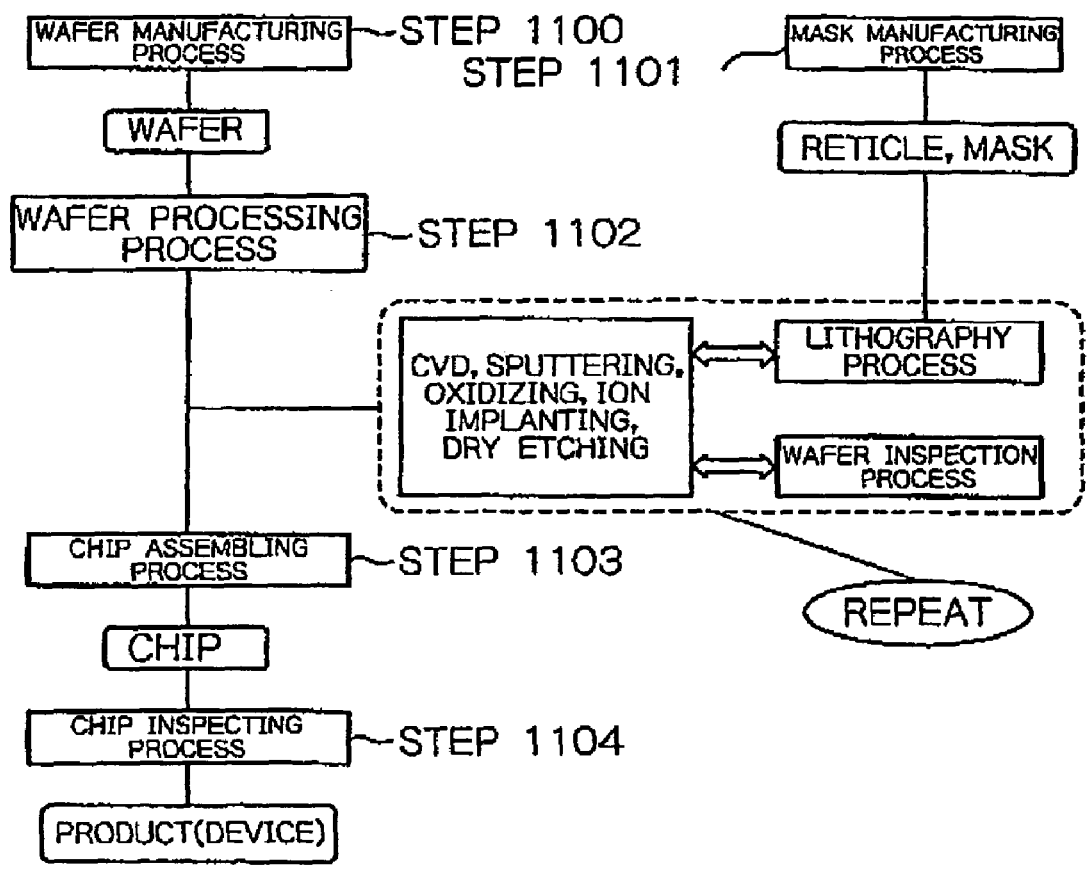
FIG. 9 is a flow chart showing a semiconductor device manufacturing process.
Figure 10:
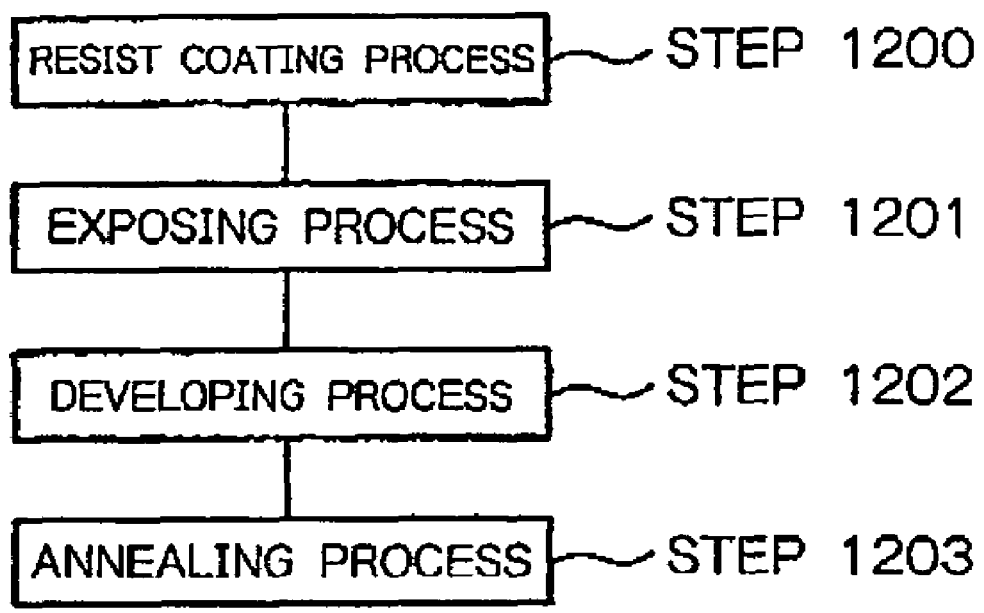
FIG. 10 is a flow chart showing a lithography process included in the semiconductor device manufacturing process of FIG. 9.

With reference to FIGS. 9 and 10, a method for manufacturing a semiconductor device by using the electron beam apparatus as illustrated in the above respective embodiments will now be described as an eleventh embodiment of the present invention.

FIG. 9 is a flow chart showing an embodiment of a manufacturing method of a semiconductor device according to the present invention. The manufacturing process in this embodiment includes the following main processes.

(1) A wafer manufacturing process for manufacturing a wafer (or wafer preparing process for preparing a wafer). (Step 1100)

(2) A mask manufacturing process for fabricating a mask to be used in the exposure (or a mask preparing process for preparing a mask). (Step 1101)

(3) A wafer processing process for performing any processing treatments necessary for the wafer. (Step 1102)

(4) A chip assembling process for cutting out those chips formed on the wafer one by one to make them operative. (Step 1103)

(5) A chip inspection process for inspecting an assembled chip. (Step 1104)

It is to be appreciated that each of those main processes further comprises several sub-processes.

Among those main processes, one that gives a critical affection to the performance of the semiconductor device is (3) the wafer processing process. In this wafer processing process, the designed circuit patterns are deposited on the wafer one on another, thus to form many chips, which will function as memories or MPUs. This wafer processing process includes the following sub-processes.

(A) A thin film deposition process for forming a dielectric thin film to be used as an insulation layer, a metallic thin film to be formed into a wiring section or an electrode section, and the like (by using the CVD process or the sputtering).

(B) An oxidizing process for oxidizing these thin film layers and the wafer substrate.

(C) A lithography process for forming a resist pattern by using a mask (reticle) in order to selectively process the thin film layers and/or the wafer substrate.

(D) An etching process for processing the thin film layer and/or the wafer substrate in conformity to the resist pattern (by using, for example, the dry etching technology).

(E) An ions/impurities implant and diffusion process.

(F) A resist stripping process.

(G) An inspection process for inspecting the processed wafer.

It is to be noted that the wafer processing process must be performed repeatedly as desired depending on the number of layers contained in the wafer, thus to manufacture the device that will be able to operate as designed.

A flow chart of FIG. 10 shows the lithography process included as a core process in said wafer processing process. The lithography process comprises the respective processes as described below.

(a) A resist coating process for coating the wafer having a circuit pattern formed thereon in the preceding stage with the resist. (Step 1200)

(b) An exposing process for exposing the resist. (Step 201)

(c) A developing process for developing the exposed resist to obtain the pattern of the resist. (Step 1202)

(d) An annealing process for stabilizing the developed pattern. (Step 1203)

All of the semiconductor device manufacturing process, the wafer processing process, and the lithography process described above are well-known, and so any further description on them should not be necessary.

When an electron beam apparatus according to the present invention is used in the above-described inspection process of (G), any defects can be detected with high throughput even on a semiconductor device having a fine pattern, enabling the 100-percent inspection and thus the improvement in yield of the products.

Although the present invention has been described and illustrated in the above detailed description of the embodiments and the drawings, it is to be understood that the present is not limited to those embodiments but they may be modified arbitrarily and preferably without departing from the scope of the present invention.

Further, any features in respective embodiments in the detailed description may be incorporated in other embodiments within a feasible range.

Although the semiconductor wafer has been taken by way of example as the sample in the above description, it is to be appreciated that the sample is not limited to that but any type of samples having a pattern and the likes on which a defect can be detected by an electron beam apparatus may be a subject to be evaluated, including a mask, for example.

What is claimed is:

1. An electron beam apparatus comprising:
an electron irradiation optics for irradiating a plurality of primary electron beams onto a sample surface;
a scanning deflector for performing a scanning operation with said plurality of primary electron beams across the sample surface;
a beam separator for separating secondary electron beams emanating from respective scanned regions on the sample from said primary electron beam;

a magnifying electron lens for magnifying a distance between any two beams of the plurality of secondary electron beams that have been separated by said beam separator;

an optical output converter for converting the plurality of magnified secondary electron beams to optical signals;

a photoelectric conversion device for converting said optical signal to an electric signal;

an optical magnifying lens for magnifying said optical signal from said optical output converter into an image on said photoelectric conversion device; and a multi-aperture plate disposed in front of said photoelectric conversion device and having a plurality of apertures formed therethrough, said aperture having an aperture area that is large in a peripheral region.

2. An electron beam apparatus comprising:

an irradiation optical system for focusing a primary electron beams onto a sample surface via an objective lens;

an image projection optical system including at least two-stage of deflectors, an magnifying lens and an aperture for detecting secondary electrons emanating from the sample;

a wobbler application circuit for applying a wobbler to an exciting or an excitation voltage of said magnifying lens subject to axial alignment;

an image formation system for forming an image separated by the wobbler in synchronization with the x- and y-directional scanning according to a signal from the electron beam transmitted through said aperture, while carrying out the x- and y-directional scanning by at least one of the deflectors in the at least two-stage of deflectors; and a deflector controller operable to control the other one of said at least two-stage of deflectors to minimize the separation of the image for the purpose of adjusting the optical axis so that a principal ray having exited from said objective lens is directed through a central region of said magnifying lens and through said aperture.

3. An electron beam apparatus comprising:

an irradiation optical system for focusing a primary electron beam onto a sample surface via an objective lens;

an image projection optical system for focusing secondary electrons emanating from the sample into an image on a detection surface, said image projection optical system having at least two-stage of deflectors, a magnifying lens and an aperture;

an optical output converter for converting the secondary electron image formed by said image projection optical system to an optical signal;

an optical member for extracting said optical signal into an atmosphere side, in which a plane disposed in a vacuum side of said optical member defines an optical output converter and an output surface of the optical signal disposed in the atmosphere side defines a curved surface;

a wobbler application circuit for applying a wobbler to an exciting or an excitation voltage of said magnifying lens subject to axial alignment;

an image formation system for forming an image separated by the wobbler in synchronization with the x- and y-directional scanning according to a signal from the electron beam transmitted through said aperture, while carrying out the x- and y-directional scanning by at least one of the deflectors in the at least two-stage of deflectors; and a deflector controller operable to control the other one of said at least two-stage of deflectors to minimize the separation of the image for the purpose of adjusting the optical axis so that a principal ray having exited from said objective lens is directed through a central region of said magnifying lens and through said aperture.

4. An electron beam apparatus comprising:

an irradiation optical system for focusing a primary electron beam onto a sample surface via an objective lens;

an image projection optical system for focusing secondary electrons emanating from the sample into an image on a detection surface;

an optical output converter for converting the secondary electron image formed by said image projection optical system to an optical signal;

an optical member for extracting said optical signal into an atmosphere side, in which a plane disposed in a vacuum side of said optical member defines an optical output converter and an output surface of the optical signal disposed in the atmosphere side defines a curved surface;

wherein said objective lens comprises:

a magnetic lens including an inner magnetic pole and an outer magnetic pole with a magnetic gap produced by said inner and said outer magnetic poles defined in the sample side; a pipe made of ferrite and disposed inside said inner magnetic pole; and a deflector disposed inside said pipe made of ferrite.

5. An objective lens for focusing an electron beam onto a sample surface, comprising:

a magnetic lens including an inner magnetic pole and an outer magnetic pole with a magnetic gap produced by said inner and said outer magnetic poles defined in the sample side;

a substantially cylindrical pipe made of ferrite and disposed inside said inner magnetic pole; and a deflector disposed inside said pipe made of ferrite.

* * * * *

UNITED STATES PATENT AND TRADEMARK OFFICE
CERTIFICATE OF CORRECTION

| | |
|---|---|
| PATENT NO. | : 7,385,197 B2 |
| APPLICATION NO. | : 11/175390 |
| DATED | : June 10, 2008 |
| INVENTOR(S) | : Mamoru Nakasuji et al. |

Page 1 of 1

It is certified that error appears in the above-identified patent and that said Letters Patent is hereby corrected as shown below:

On the Title Page:

In item (75) change "Masahiro Hatakayama" to be --Masahiro Hatakeyama--.

Signed and Sealed this

Sixteenth Day of September, 2008

JON W. DUDAS
*Director of the United States Patent and Trademark Office*